(12) United States Patent
Chen et al.

(10) Patent No.: US 11,345,648 B2
(45) Date of Patent: May 31, 2022

(54) HALOGENATED CONJUGATED DIENE COMPOUND, AND PREPARATION AND APPLICATION THEREOF

(71) Applicant: ORIENTAL(LUZHOU) AGROCHEMICALS CO., LTD., Sichuan (CN)

(72) Inventors: Bangchi Chen, Sichuan (CN); Yinwei Sun, Sichuan (CN); Zhongyuan Wang, Sichuan (CN); Miao Lin, Sichuan (CN)

(73) Assignee: ORIENTAL(LUZHOU) AGROCHEMICALS CO., LTD., Luzhou (CN)

( * ) Notice: Subject to any disclaimer, the term of this patent is extended or adjusted under 35 U.S.C. 154(b) by 0 days.

(21) Appl. No.: 17/489,596

(22) Filed: Sep. 29, 2021

(65) Prior Publication Data

US 2022/0017437 A1    Jan. 20, 2022

Related U.S. Application Data

(63) Continuation of application No. PCT/CN2019/080822, filed on Apr. 1, 2019.

(51) Int. Cl.
*C07C 17/06* (2006.01)
*C07C 23/10* (2006.01)
*C07C 231/06* (2006.01)
*C07C 255/31* (2006.01)

(52) U.S. Cl.
CPC ............ *C07C 17/06* (2013.01); *C07C 23/10* (2013.01); *C07C 231/06* (2013.01); *C07C 255/31* (2013.01); *C07C 2601/14* (2017.05)

(58) Field of Classification Search
None
See application file for complete search history.

(56) References Cited

U.S. PATENT DOCUMENTS 4,293,626 A    10/1981    Webster et al.

FOREIGN PATENT DOCUMENTS

| CN | 102336686 A | 2/2012 | |
| CN | 108264469 A | 7/2018 | |
| DE | 277672 A1 * | 4/1990 | ........... C07C 149/26 |
| WO | 9947525 A1 | 9/1999 | |
| WO | 0117352 A1 | 3/2001 | |
| WO | 2007073933 A2 | 7/2007 | |
| WO | 2008049618 A2 | 5/2008 | |

OTHER PUBLICATIONS

Patent DD277672A1, Abstract English translation, Nov. 4, 1990, pp. 1-2. (Year: 1990).*

* cited by examiner

*Primary Examiner* — Medhanit W Bahta

(57) ABSTRACT

Disclosed are a type of halogenated conjugated diene compounds (1), and preparation and application thereof. In this method, a conjugated diene compounds is subjected to halogenation reaction to prepare the compound (1). This disclosure further provides a method of preparing a 2-arylmalonic acid derivative from the compound (1) through dehydrohalogenation and aromatization reaction.

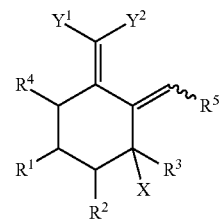

10 Claims, No Drawings

HALOGENATED CONJUGATED DIENE COMPOUND, AND PREPARATION AND APPLICATION THEREOF

CROSS-REFERENCE TO RELATED APPLICATIONS

This application is a continuation of International Patent Application No. PCT/CN2019/080822, filed on Apr. 1, 2019. The content of the aforementioned applications, including any intervening amendments thereto, is incorporated herein by reference in its entirety.

TECHNICAL FIELD

This application relates to organic synthesis, and more particularly to a halogenated conjugated diene compound, and a preparation and application thereof.

BACKGROUND

Provided herein is a type of novel halogenated conjugated diene compounds of formula (1):

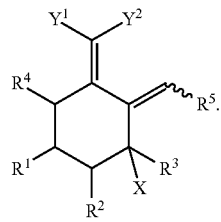

Compounds (1) with multifunctional groups, after further functional group transformations are expected to be useful in the synthesis of a variety of derivatives with different chemical properties, physical properties, and biological activities, these derivatives can be used to produce final products with practical application values, such as the herbicide [8-(2,6-diethyl-4-methylphenyl)-7-oxo-1,2,4,5-tetrahydro-7H-pyrazolo[1,2-d][1,4,5]o xadiazepin-9-yl]2,2-dimethylpropanoate (Pinoxaden). The application of this herbicide has been disclosed by International Patent Publication Nos. WO 9947525, WO 0117352, WO 2007073933 and WO 2008049618.

However, these structurally novel compounds (1) have not been reported yet.

SUMMARY

A first object of this application is to provide a halogenated conjugated diene compound of formula (1)

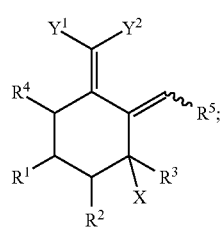

wherein:
$R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen and sulfur;

$Y^1$ and $Y^2$ each are independently a cyano group or —$COR^6$, where the $R^6$ is hydrogen, a $C_1$-$C_{10}$ alkyl group, a $C_1$-$C_{10}$ alkoxy group, a $C_6$-$C_{12}$ aryloxy group, an amino group, a $C_1$-$C_{10}$ alkylamino group, a $C_6$-$C_{12}$ arylamino group, a di($C_1$-$C_{10}$ alkyl) amino group, a ($C_1$-$C_{10}$ alkyl)($C_6$-$C_{12}$ aryl) amino group, a di($C_6$-$C_{12}$ aryl) amino group, a $C_6$-$C_{12}$ aryl group or a heteroaryl group containing one or two atoms selected from nitrogen, oxygen and sulfur; and X is halogen.

In an embodiment, $R^1$, $R^2$, $R^3$, $R^4$ and $R^5$ each are independently hydrogen, a $C_1$-$C_4$ alkyl group or a $C_6$-$C_{12}$ aryl group.

In an embodiment, $Y^1$ and $Y^2$ each are independently a cyano group, —COOMe, —COOEt or —$CONH_2$.

In an embodiment, X is chlorine or bromine.

A second object of this application is to provide a method for preparing the halogenated conjugated diene compound (1), comprising:

halogenating compound (2) in the presence of a halogenating agent to obtain the compound (1), as shown in the following reaction scheme:

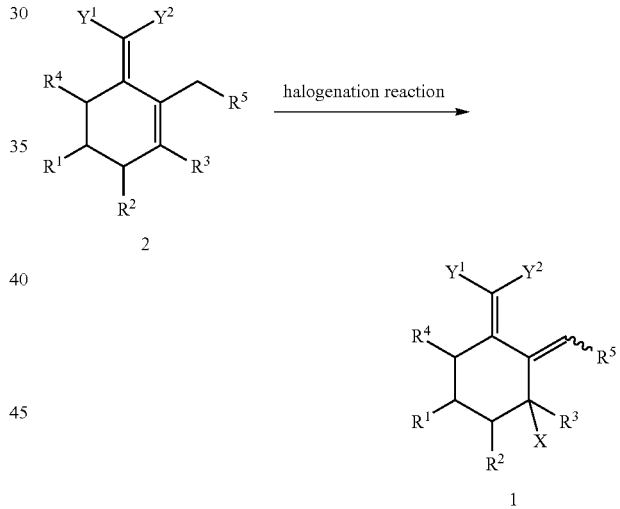

wherein:
$R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen and sulfur;

$Y^1$ and $Y^2$ each are independently a cyano group or —$COR^6$, where the $R^6$ is hydrogen, a $C_1$-$C_{10}$ alkyl group, a $C_1$-$C_{10}$ alkoxy group, a $C_6$-$C_{12}$ aryloxy group, an amino group, a $C_1$-$C_{10}$ alkylamino group, a $C_6$-$C_{12}$ arylamino group, a di($C_1$-$C_{10}$ alkyl) amino group, a ($C_1$-$C_{10}$ alkyl)($C_6$-$C_{12}$ aryl) amino group, a di($C_6$-$C_{12}$ aryl) amino group, a $C_6$-$C_{12}$ aryl group or a heteroaryl group containing one or two atoms selected from nitrogen, oxygen and sulfur; and X is halogen.

In an embodiment, $R^1$, $R^2$, $R^3$, $R^4$ and $R^5$ each are independently hydrogen, a $C_1$-$C_4$ alkyl group or a $C_6$-$C_{12}$ aryl group.

In an embodiment, $Y^1$ and $Y^2$ each are independently a cyano group, —COOMe, —COOEt or —CONH$_2$.

In an embodiment, X is chlorine or bromine.

In an embodiment, the halogenating agent is selected from the group consisting of an elemental halogen (such as chlorine gas and liquid bromine), a hypohalous acid (such as hypochlorous acid and hypobromous acid), a sulfonyl halide (such as sulfuryl chloride), a thionyl halide (such as thionyl chloride) and a mixture thereof, preferably chlorine gas, sulfuryl chloride or liquid bromine.

A third object of this application is to provide a method of preparing a compound (3), comprising:

subjecting compound (1) to dehydrohalogenation and aromatization reactions to produce the compound (3), as shown in the following reaction scheme:

[Reaction scheme showing compound 1 (cyclohexylidene with Y¹, Y², R¹-R⁵, X substituents) undergoing dehydrohalogenation and aromatization to give compound 3 (benzene ring with Y¹, Y², R¹-R⁵ substituents)]

wherein:
$R^1$, $R^2$, $R^3$, $R^4$ and $R^5$ each are independently hydrogen, a $C_1$-$C_{10}$ alkyl group, a $C_6$-$C_{12}$ aryl group or a heteroaryl group containing one or two atoms selected from nitrogen, oxygen and sulfur;

$Y^1$ and $Y^2$ each are independently a cyano group or —COR$^6$, where the $R^6$ is hydrogen, a $C_1$-$C_{10}$ alkyl group, a $C_1$-$C_{10}$ alkoxy group, a $C_6$-$C_{12}$ aryloxy group, an amino group, a $C_1$-$C_{10}$ alkylamino group, a $C_6$-$C_{12}$ arylamino group, a di($C_1$-$C_{10}$ alkyl) amino group, a ($C_1$-$C_{10}$ alkyl)($C_6$-$C_{12}$ aryl) amino group, a di($C_6$-$C_{12}$ aryl) amino group, a $C_6$-$C_{12}$ aryl group or a heteroaryl group containing one or two atoms selected from nitrogen, oxygen and sulfur; and X is halogen.

In an embodiment, $R^1$, $R^2$, $R^3$, $R^4$ and $R^5$ each are independently hydrogen, a $C_1$-$C_4$ alkyl group or a $C_6$-$C_{12}$ aryl group.

In an embodiment, $Y^1$ and $Y^2$ each are independently a cyano group, —COOMe, —COOEt or —CONH$_2$.

In an embodiment, X is chlorine or bromine.

In an embodiment, the dehydrohalogenation and aromatization reactions are carried out in the presence of a catalyst, where the catalyst is an alkali metal halide, an alkali earth metal halide or a combination thereof, preferably lithium chloride or sodium chloride.

In an embodiment, a molar ratio of the catalyst to the compound (1) is (0.005-2.4):1, preferably (0.02-0.1): 1.

In an embodiment, the dehydrohalogenation and aromatization reactions are performed at 0-150° C., preferably 110-150° C.

The inventors of the present application have also found that it is not necessary to separate the intermediate produced in the preparation of the compound (1), and the compound (3) can be directly obtained in a one-pot manner.

In an embodiment, 2-(3-chloro-6-ethyl-2-ethylene-4-methyl-1-cyclohexylidene) malononitrile (namely, $R^1$ and $R^3$ are hydrogen, $R^2$ and $R^5$ are methyl, $R^4$ is ethyl; $Y^1$ and $Y^2$ are cyano; and X is chlorine) and/or a 2-(2,6-diethyl-4-methylphenyl) malononitrile (namely, $R^1$ and $R^3$ are hydrogen, $R^2$ and $R^5$ are methyl, $R^4$ is ethyl; and $Y^1$ and $Y^2$ are cyano) produced by the method provided herein can undergo further conversion and reaction to prepare the herbicide [8-(2,6-diethyl-4-methylphenyl)-7-oxo-1,2,4,5-tetrahydro-7H-pyrazolo[1,2-d][1,4,5]oxadiazepin-9-yl]2,2-dimethyl-propanoate (Pinoxaden).

Compared to the prior art, this application has the following beneficial effects.

(1) This application provides a type of structurally novel halogenated conjugated diene compounds (1) and a preparation method thereof.

(2) The halogenated conjugated diene compounds (1) containing multi-functional groups can be used to synthesize other valuable compounds through further functional group transformations, such as the herbicide [8-(2,6-diethyl-4-methylphenyl)-7-oxo-1,2,4,5-tetrahydro-7H-pyrazolo[1,2-d][1,4,5]oxadiazepin-9-yl]2,2-dimethylpropanoate (Pinoxaden).

DETAILED DESCRIPTION OF EMBODIMENTS

This application will be described in detail below with reference to the embodiments to make objects, technical features and advantages of this application clearer, but these embodiments are not intended to limit the scope of this application.

The starting material 2 can be prepared by known methods in the prior art (for example, WO 2018/120094).

Example 1: Preparation of 2-(3-chloro-6-ethyl-2-ethylidene-4-methyl-1-cyclohexylidene) malononitrile To a 250 mL three-necked flask equipped with a magnetic stirrer and a thermometer were sequentially added 85.0 g of acetic acid and 42.9 g of 2-(2,6-diethyl-4-methyl-2-ene-1-cyclohexylidene) malononitrile. The reaction mixture was mixed, cooled to 15° C., and fed with chlorine gas until the reaction was complete. The reaction mixture was concentrated to give 49.7 g of 2-(3-chloro-6-ethyl-2-ethylidene-4-methyl-1-cyclohexylidene) malononitrile.

$^1$HNMR (CDCl$_3$, 400 MHz, TMS): δ 6.04 (q, J=6.0 Hz, 1H), 4.98 (d, J=1.2 Hz, 1H), 3.01-2.99 (m, 1H), 2.29-2.24 (m, 1H), 2.01-1.97 (m, 1H), 1.94 (d, J=6.0 Hz, 3H), 1.70-1.66 (m, 1H), 1.56-1.49 (m, 2H), 1.09 (d, J=4.8 Hz, 3H), 0.92 (t, J=5.6 Hz, 3H).

$^{13}$CNMR (CDCl$_3$, 125 MHz): δ 180.6, 134.6, 132.8, 112.3, 112.2, 84.4, 62.1, 44.1, 32.7, 31.1, 26.5, 18.4, 13.8, 11.5.

Example 2: Preparation of 2-(3-chloro-6-ethyl-2-ethylidene-4-methyl-1-cyclohexylidene) malononitrile To a 500 mL three-necked flask equipped with a magnetic stirrer and a thermometer were sequentially added 170.0 g of acetic acid and 43.0 g of 2-(2,6-diethyl-4-methyl-2-ene-1-cyclohexylidene) malononitrile. The reaction mixture was mixed and heated to 45° C., and 29.8 g of sulfuryl chloride was dropwise added and reacted at 45° C. for 1 h. After the reaction was complete, the reaction mixture was concentrated to give 50.0 g of 2-(3-chloro-6-ethyl-2-ethylidene-4-methyl-1-cyclohexylidene) malononitrile.

Example 3: Preparation of 2-(3-chloro-6-ethyl-2-ethylidene-4-methyl-1-cyclohexylidene) malononitrile To a 250 mL three-necked flask equipped with a magnetic stirrer and a thermometer were sequentially added 85.0 g of tetrahydrofuran and 42.9 g of 2-(2,6-diethyl-4-methyl-2-ene-1-cyclohexylidene) malononitrile. The reaction mixture was mixed. 32.7 g of 5% sodium hypochlorite solution was added, followed by slow dropwise addition of 10% hydrochloric acid to adjust pH to 3-4. Then the reaction mixture was stirred for 30 min, and ethyl acetate was added. The organic phase was washed and concentrated to give 49.7 g of 2-(3-chloro-6-ethyl-2-ethylidene-4-methyl-1-cyclohexylidene) malononitrile.

Example 4: Preparation of 2-(2,6-diethyl-4-methylphenyl) malononitrile

To a 250 mL three-necked flask equipped with a magnetic stirrer, a thermometer and a reflux condenser were sequentially added 150 g of N-methyl-2-pyrrolidone and 30.0 g of 2-(3-chloro-6-ethyl-2-ethylidene-4-methyl-1-cyclohexylidene) malononitrile provided in Example 1. The reaction mixture was mixed, and heated to 130° C. under a nitrogen atmosphere for reaction. After the reaction was complete, the reaction mixture was concentrated, washed and separated to give 28.0 g of 2-(2,6-diethyl-4-methylphenyl) malononitrile.
$^1$H NMR (CDCl$_3$, 500 MHz, TMS): δ 7.00 (s, 2H), 5.29 (s, 1H), 2.81 (q, J=7.5 Hz, 4H), 2.34 (s, 3H), 1.32 (t, J=7.5 Hz, 6H).
$^{13}$C NMR (CDCl$_3$, 125 MHz): δ 142.66, 140.73, 128.74, 120.00, 112.24, 26.48, 21.21, 21.13, 15.03.

Example 5: Preparation of 2-(2,6-diethyl-4-methylphenyl) malononitrile

To a 500 mL three-necked flask equipped with a magnetic stirrer, a thermometer and a reflux condenser were sequentially added 200 g of toluene, 49.7 g of 2-(3-chloro-6-ethyl-2-ethylidene-4-methyl-1-cyclohexylidene) malononitrile provided in Example 1 and 30.4 g of triethylamine. The reaction mixture was mixed, and refluxed until the reaction was complete. The reaction mixture was cooled, washed, concentrated and separated to give 24.0 g of 2-(2,6-diethyl-4-methylphenyl) malononitrile.

Example 6: Preparation of 2-(2,6-diethyl-4-methylphenyl) malononitrile

To a 500 mL three-necked flask equipped with a magnetic stirrer, a thermometer and a reflux condenser were sequentially added 125.0 g of chlorobenzene and 53.5 g of 2-(2,6-diethyl-4-methyl-2-ene-1-cyclohexylidene) malononitrile. The reaction mixture was mixed, cooled to 0° C., and fed with chlorine gas until the reaction was complete. The reaction mixture was desolventized, and 200 g of N,N-dimethylformamide and 0.85 g of lithium chloride (LiCl) were added, and refluxed until the reaction was complete. Then the reaction mixture was concentrated, washed and separated to give 47.2 g of 2-(2,6-diethyl-4-methylphenyl) malononitrile.

Example 7: Preparation of 2-(2,6-diethyl-4-methylphenyl) malononitrile

To a 500 mL three-necked flask equipped with a magnetic stirrer, a thermometer and a reflux condenser were sequentially added 125.0 g of chlorobenzene and 53.5 g of 2-(2,6-diethyl-4-methyl-2-ene-1-cyclohexylidene) malononitrile. The reaction mixture was mixed, cooled to 0° C., and fed with chlorine gas until the reaction was complete. The reaction mixture was desolventized, 200 g of N,N-dimethylformamide and 1.17 g of sodium chloride (NaCl) were added, and refluxed until the reaction was complete. Then the reaction mixture was concentrated, washed and separated to give 45.6 g of 2-(2,6-diethyl-4-methylphenyl) malononitrile.

Example 8: Preparation of methyl 2-cyano-2-(2,6-diethyl-4-methylphenyl) acetate To a 250 mL three-necked flask equipped with a magnetic stirrer, a thermometer and a reflux condenser were sequentially added 60.0 g of ethyl acetate and 30.0 g of methyl 2-cyano-2-(2,6-diethyl-4-methyl-2-ene-1-cyclohexylidene) acetate. The reaction mixture was mixed, cooled to 5° C., and fed with chlorine gas until the reaction was complete. The reaction mixture was desolventized, and 100 mL of N,N-dimethylformamide and 0.22 g of LiCl were added, and refluxed until the reaction was complete. The reaction mixture was concentrated, washed and separated to give 23.1 g of methyl 2-cyano-2-(2,6-diethyl-4-methylphenyl) acetate.
$^1$HNMR (CDCl$_3$, 500 MHz, TMS): δ 6.95 (s, 2H), 3.80 (s, 3H), 2.76-2.59 (m, 4H), 2.32 (s, 3H), 1.24 (t, J=9.5 Hz, 6H).
$^{13}$CNMR (CDCl$_3$, 125 MHz): δ 166.5, 142.8, 139.2, 128.2, 123.9, 115.9, 53.7, 36.8, 26.3, 21.1, 15.0.

Example 9: Preparation of 2-(2,6-diethyl-4-methylphenyl) malononitrile

To a 250 mL three-necked flask equipped with a magnetic stirrer, a thermometer and a reflux condenser were sequentially added 85.0 g of acetic acid and 21.5 g of 2-(2,6-diethyl-4-methyl-2-ene-1-cyclohexylidene) malononitrile. The reaction mixture was mixed, heated to 45° C., 60 g of a solution of 17.6 g of liquid bromine in acetic acid was dropwise added, and reacted at 45° C. for 2 h. The reaction mixture was desolventized, 100 g of N,N-dimethylformamide and 0.95 g of lithium bromide (LiBr) were added, and refluxed until the reaction was complete. The reaction mixture was concentrated, washed and separated to give 9.3 g of 2-(2,6-diethyl-4-methylphenyl) malononitrile.

Example 10: Preparation of 2-(2,6-diethyl-4-methylphenyl) malonamide

To a 100 mL three-necked flask equipped with a magnetic stirrer and a thermometer were sequentially added 3.6 g of water and 50.0 g of concentrated sulfuric acid. The reaction mixture was mixed, heated to 45° C., and followed by slowly addition of 21.1 g of 2-(2,6-diethyl-4-methylphenyl) malononitrile. The reaction mixture was reacted under stirring at 50° C. for 5 h, cooled, poured into an ice water and ethyl acetate was added. The organic phase was combined, dried and concentrated to give 24.1 g of 2-(2,6-diethyl-4-methylphenyl) malonamide.

Example 11 Preparation of Pinoxaden

To a 250 mL three-necked flask equipped with a magnetic stirrer, a thermometer and a reflux condenser were sequentially added 24.8 g of 2-(2,6-diethyl-4-methylphenyl) malonamide provided in Example 10, 21.0 g of [1,4,5]-oxadiazepine dihydrochloride, 125.0 g of chlorobenzene and 40.4 g of triethylamine, and then refluxed until the reaction was complete. The reaction mixture was cooled to room temperature, followed by slowly addition of 21.6 g of pivaloyl chloride and reacted at room temperature under stirring for 2 h. The reaction mixture was added with diluted hydrochloric acid to adjust pH to 3-4, and ethyl acetate was added. The organic phase was combined, dried, concentrated and crystallized with hexane to give 29.6 g of Pinoxaden.

1HNMR (CDCl$_3$, 500 MHz, TMS): δ 8.88 (s, 2H), 4.28-4.26 (m, 2H), 3.94-3.93 (m, 2H), 3.89-3.83 (m, 4H), 2.56-2.47 (m, 2H), 2.45-2.40 (m, 2H), 2.39 (s, 3H), 1.12 (t, J=9.0 Hz, 3H), 1.23 (s, 9H).

What is claimed is:

1. A halogenated conjugated diene compound of formula (1),

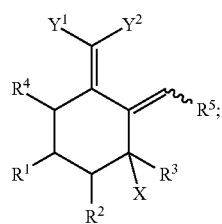

1 wherein:
R$^1$, R$^2$, R$^3$, R$^4$ and R$^5$ each are independently hydrogen, a C$_1$-C$_{10}$ alkyl group, a C$_6$-C$_{12}$ aryl group or a heteroaryl group containing one or two atoms selected from nitrogen, oxygen and sulfur;
Y$^1$ and Y$^2$ each are independently a cyano group or —COR$^6$, where the R$^6$ is hydrogen, a C$_1$-C$_{10}$ alkyl group, a C$_1$-C$_{10}$ alkoxy group, a C$_6$-C$_{12}$ aryloxy group, an amino group, a C$_1$-C$_{10}$ alkylamino group, a C$_6$-C$_{12}$ arylamino group, a di(C$_1$-C$_{10}$ alkyl) amino group, a (C$_1$-C$_{10}$ alkyl)(C$_6$-C$_{12}$ aryl) amino group, a di(C$_6$-C$_{12}$ aryl) amino group, a C$_6$-C$_{12}$ aryl group or a heteroaryl group containing one or two atoms selected from nitrogen, oxygen and sulfur; and
X is halogen.

2. The halogenated conjugated diene compound of claim 1, wherein R$^1$, R$^2$, R$^3$, R$^4$ and R$^5$ each are independently hydrogen, a C$_1$-C$_4$ alkyl group or a C$_6$-C$_{12}$ aryl group; Y$^1$ and Y$^2$ each are independently a cyano group, —COOMe, —COOEt or —CONH$_2$; and X is chlorine or bromine.

3. A method for preparing a halogenated conjugated diene compound of formula (1), comprising:
subjecting compound (2) to halogenation in the presence of a halogenating agent to obtain the halogenated conjugated diene compound (1), as shown in the following reaction scheme:

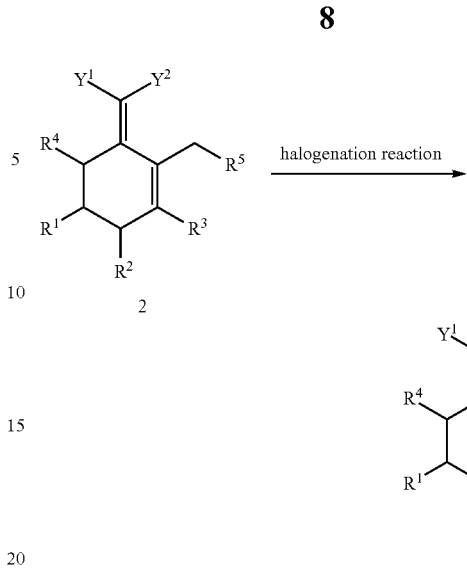

wherein:
R$^1$, R$^2$, R$^3$, R$^4$ and R$^5$ each are independently hydrogen, a C$_1$-C$_{10}$ alkyl group, a C$_6$-C$_{12}$ aryl group or a heteroaryl group containing one or two atoms selected from nitrogen, oxygen and sulfur;
Y$^1$ and Y$^2$ each are independently a cyano group or —COR$^6$, where the R$^6$ is hydrogen, a C$_1$-C$_{10}$ alkyl group, a C$_1$-C$_{10}$ alkoxy group, a C$_6$-C$_{12}$ aryloxy group, an amino group, a C$_1$-C$_{10}$ alkylamino group, a C$_6$-C$_{12}$ arylamino group, a di(C$_1$-C$_{10}$ alkyl) amino group, a (C$_1$-C$_{10}$ alkyl)(C$_6$-C$_{12}$ aryl) amino group, a di(C$_6$-C$_{12}$ aryl) amino group, a C$_6$-C$_{12}$ aryl group or a heteroaryl group containing one or two atoms selected from nitrogen, oxygen and sulfur; and
X is halogen.

4. The method of claim 3, wherein the halogenating agent is an elemental halogen, a hypohalous acid, a sulfonyl halide, a thionyl halide or a combination thereof.

5. The method of claim 4, wherein the halogenating agent is chlorine gas, sulfuryl chloride or liquid bromine.

6. A method of preparing a 2-aryl malonic acid derivative of formula (3), comprising:
subjecting compound (1) to dehydrohalogenation and aromatization reactions to obtain the 2-aryl malonic acid derivative (3), as shown in the following reaction scheme:

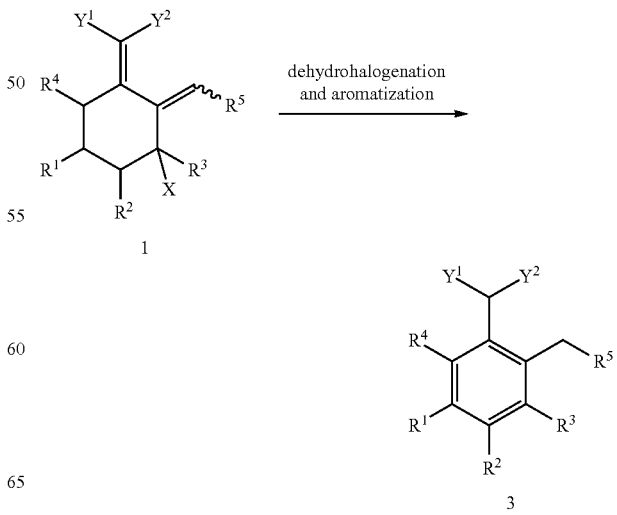

wherein:

R$^1$, R$^2$, R$^3$, R$^4$ and R$^5$ each are independently hydrogen, a C$_1$-C$_{10}$ alkyl group, a C$_6$-C$_{12}$ aryl group or a heteroaryl group containing one or two atoms selected from nitrogen, oxygen and sulfur;

Y$^1$ and Y$^2$ each are independently a cyano group or —COR$^6$, where the R$^6$ is hydrogen, a C$_1$-C$_{10}$ alkyl group, a C$_1$-C$_{10}$ alkoxy group, a C$_6$-C$_{12}$ aryloxy group, an amino group, a C$_1$-C$_{10}$ alkylamino group, a C$_6$-C$_{12}$ arylamino group, a di(C$_1$-C$_{10}$ alkyl) amino group, a (C$_1$-C$_{10}$ alkyl)(C$_6$-C$_{12}$ aryl) amino group, a di(C$_6$-C$_{12}$ aryl) amino group, a C$_6$-C$_{12}$ aryl group or a heteroaryl group containing one or two atoms selected from nitrogen, oxygen and sulfur; and X is halogen.

7. The method of claim 6, wherein the dehydrohalogenation and aromatization reactions are performed at 0-150° C.; the dehydrohalogenation and aromatization reactions are carried out in the presence of a catalyst; the catalyst is an alkali metal halide, an alkali earth metal halide or a combination thereof; and a molar ratio of the catalyst to the compound (1) is (0.005-2.4):1.

8. The method of claim 7, wherein the dehydrohalogenation and aromatization reactions are performed at 110-150° C.; the catalyst is lithium chloride or sodium chloride; and the molar ratio of the catalyst to the compound (1) is (0.02-0.1):1.

9. The method of claim 6, wherein an intermediate in a preparation of the compound (1) is not separated, and the 2-aryl malonic acid derivative (3) is obtained in a one-pot manner.

10. A method of synthesizing [8-(2,6-diethyl-4-methylphenyl)-7-oxo-1,2,4,5-tetrahydro-7H-pyrazolo[1,2-d][1,4,5]o xadiazepin-9-yl]2,2-dimethylpropanoate, comprising:

subjecting 2-(3-chloro-6-ethyl-2-ethylidene-4-methyl-1-cyclohexylidene)malononitrile to dehydrohalogenation and aromatization reactions in the presence of a catalyst to obtain 2-(2,6-diethyl-4-methylphenyl) malononitrile;

reacting the 2-(2,6-diethyl-4-methylphenyl) malononitrile in the presence of concentrated sulfuric acid to obtain 2-(2,6-diethyl-4-methylphenyl) malonamide; and subjecting the 2-(2,6-diethyl-4-methylphenyl) malonamide, [1,4,5]-oxadiazepine dihydrochloride and pivaloyl chloride to reaction in the presence of triethylamine to obtain [8-(2,6-diethyl-4-methylphenyl)-7-oxo-1,2,4,5-tetrahydro-7H-pyrazolo[1,2-d][1,4,5]o xadiazepin-9-yl]2,2-dimethylpropanoate, as shown in the following reaction scheme:

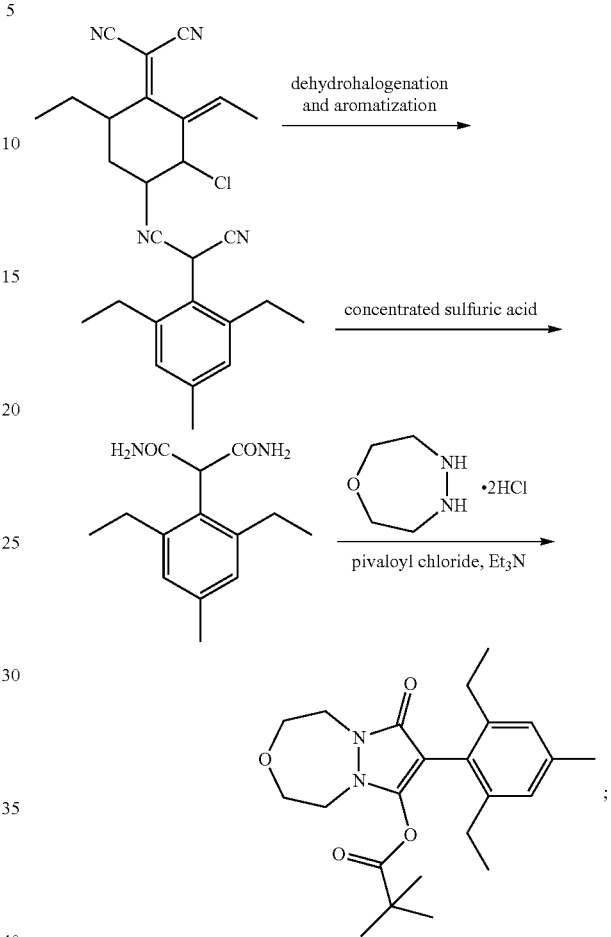

wherein the catalyst is selected from the group consisting of an alkali metal halide, an alkaline earth metal halide and a mixture thereof.

* * * * *